US006936001B1

(12) United States Patent
Snow

(10) Patent No.: US 6,936,001 B1
(45) Date of Patent: Aug. 30, 2005

(54) HEART STABILIZER

(75) Inventor: Edward Ramsey Snow, Santa Barbara, CA (US)

(73) Assignee: Computer Motion, Inc., Sunnyvale, CA (US)

( * ) Notice: Subject to any disclaimer, the term of this patent is extended or adjusted under 35 U.S.C. 154(b) by 0 days.

(21) Appl. No.: 09/411,442

(22) Filed: Oct. 1, 1999

(51) Int. Cl.$^7$ ................................................ A61F 2/00
(52) U.S. Cl. ......................... 600/37; 600/201; 600/235
(58) Field of Search ........................ 600/37, 201, 204, 600/215, 216, 219, 210, 235

(56) References Cited

U.S. PATENT DOCUMENTS

| | | | | |
|---|---|---|---|---|
| 5,865,730 A | * | 2/1999 | Fox et al. ................... 600/201 |
| 5,894,843 A | * | 4/1999 | Benetti et al. ............... 600/201 |
| 5,927,284 A | * | 7/1999 | Borst et al. .................. 600/201 |
| 6,063,021 A | * | 5/2000 | Hossain et al. ............... 600/37 |
| 6,248,062 B1 | * | 6/2001 | Adler et al. ................. 600/204 |

* cited by examiner

Primary Examiner—John P. Lacyk
(74) Attorney, Agent, or Firm—Townsend and Townsend and Crew LLP; Lynn M. Thompson

(57) ABSTRACT

A heart stabilizer that may include a wrist which couples an end effector to a first linkage. The end effector and wrist may be inserted through an incision in the chest of a patient to assist in performing a minimally invasive coronary procedure. The wrist provides dexterity so that the end effector can be placed on the heart to stabilize the same.

31 Claims, 8 Drawing Sheets

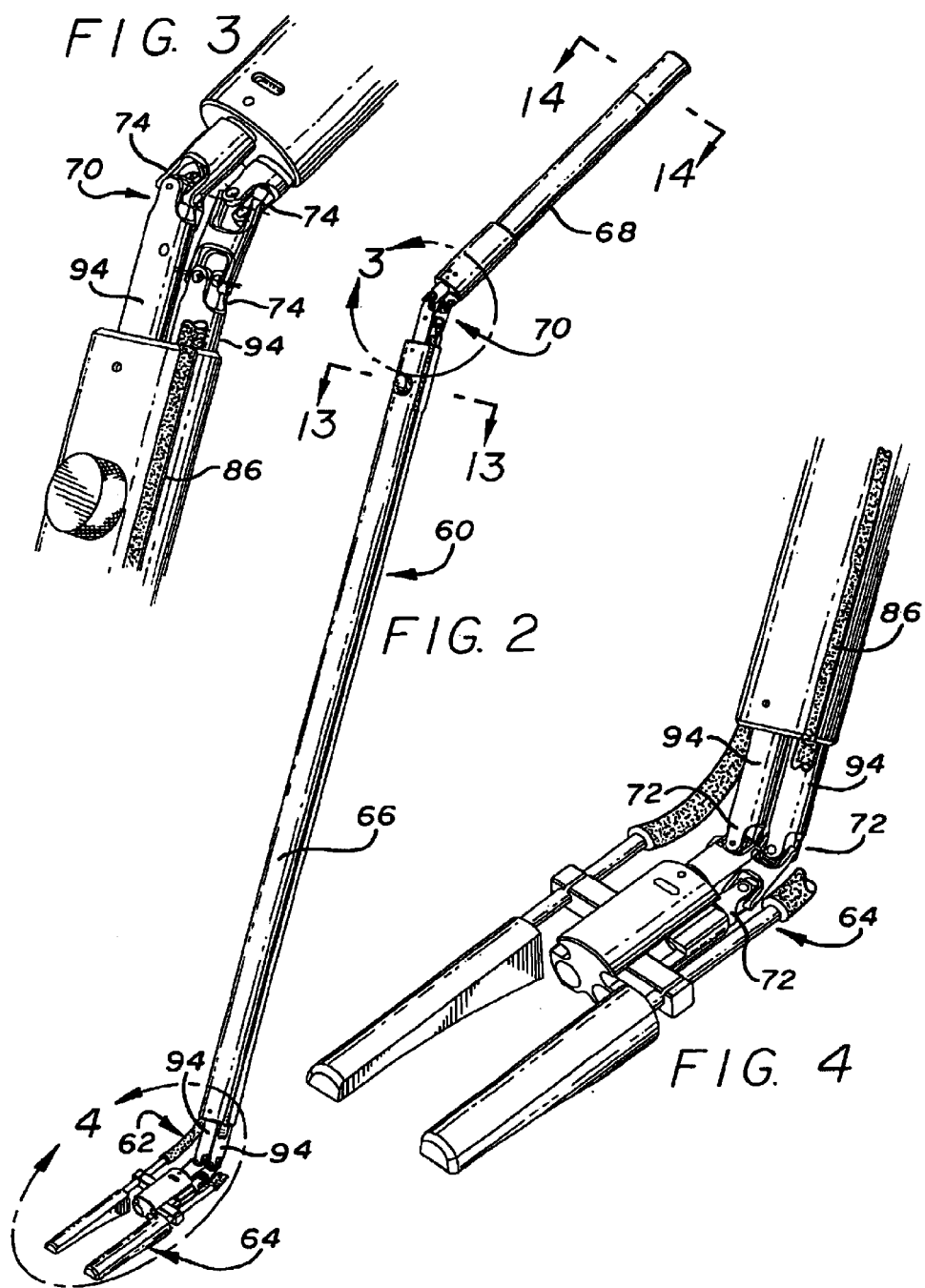

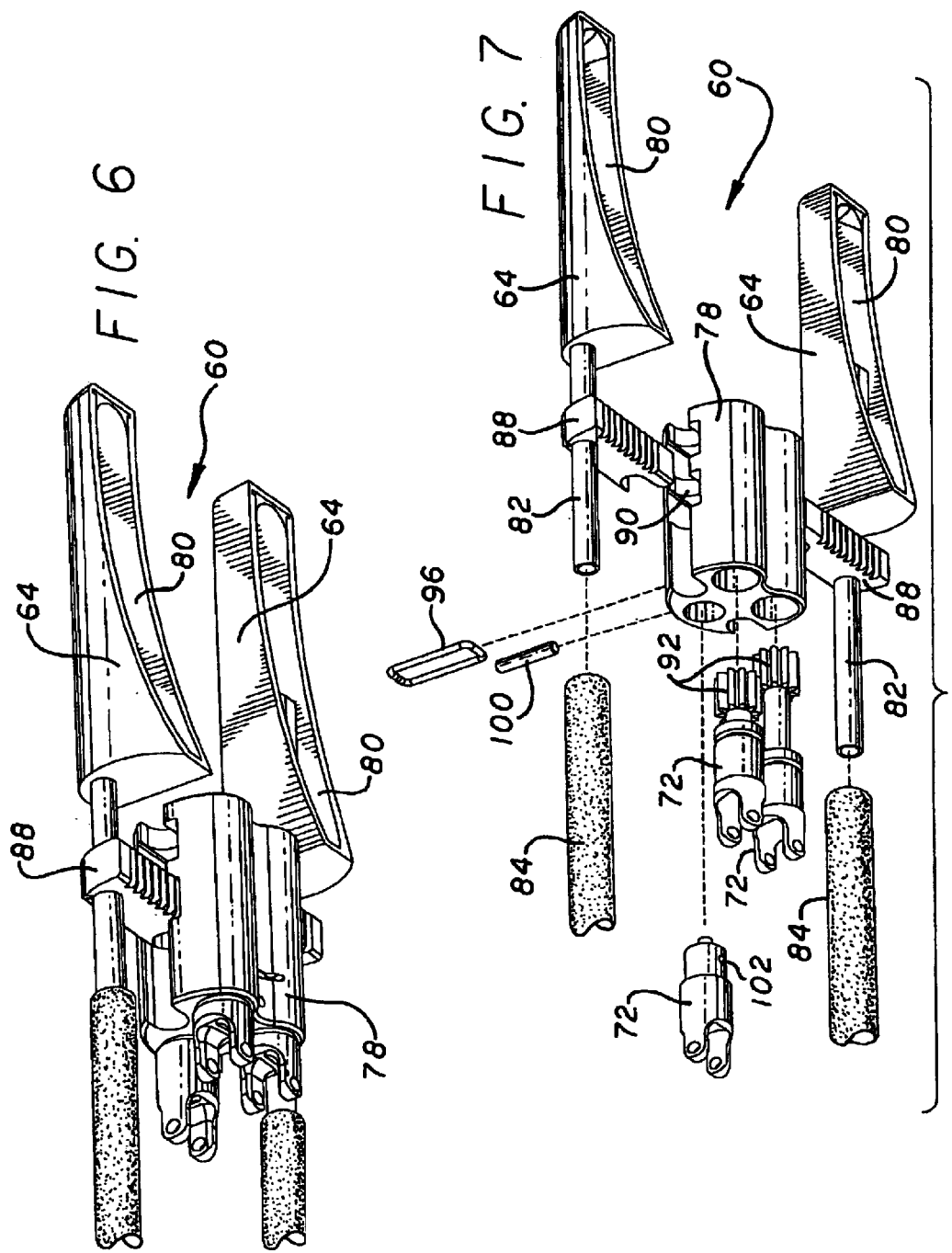

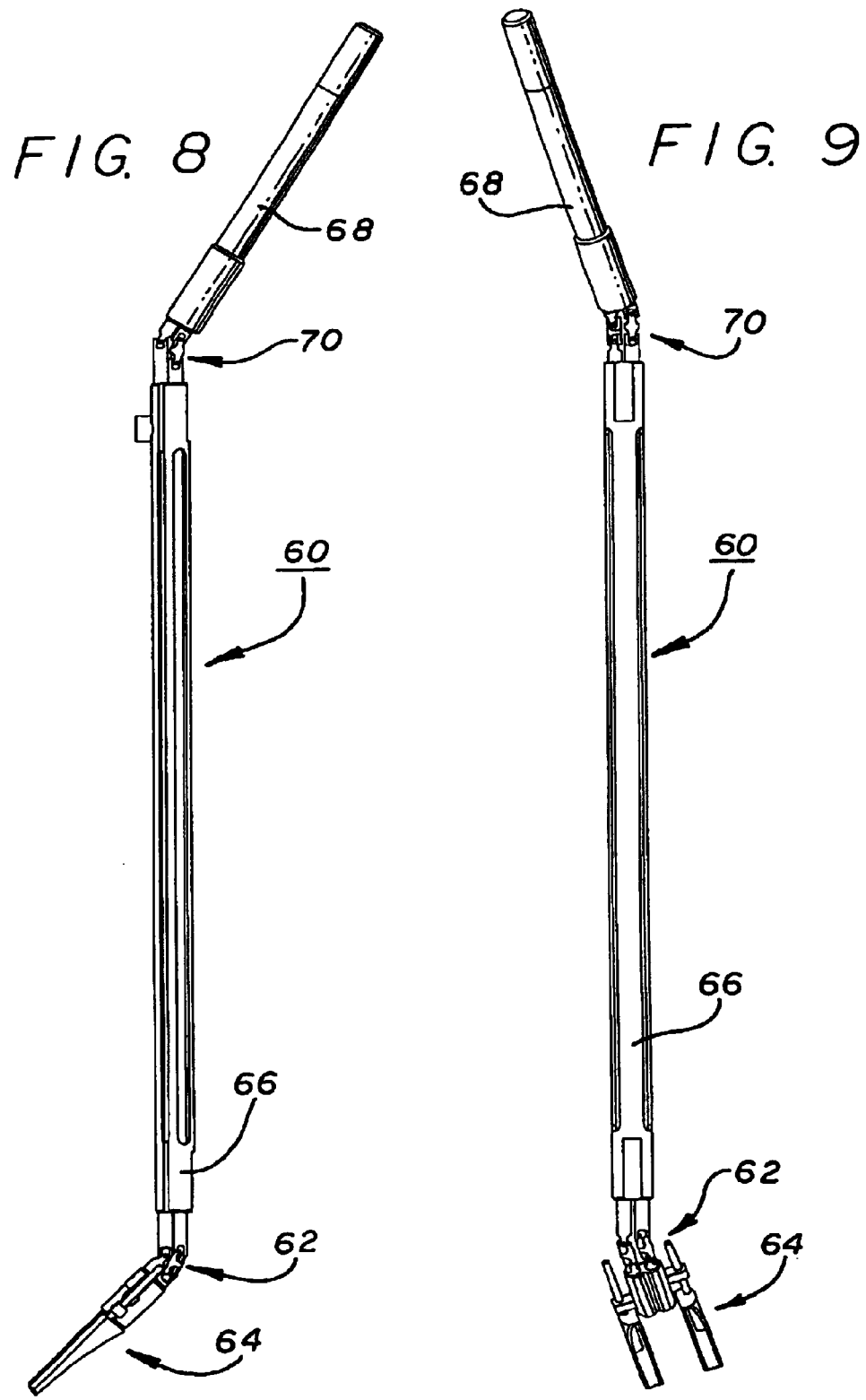

HEART STABILIZER

BACKGROUND OF THE INVENTION

1. Field of the Invention

The present invention relates to an articulate heart stabilizer.

2. Background Information

Blockage of a coronary artery may deprive the heart of blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery is then severed and attached to the artery at the point of incision. The internal mammary artery bypasses the blocked area of the artery to again provide a full flow of blood to the heart. Splitting the sternum and opening the chest cavity can create a tremendous trauma to the patient. Additionally, the cracked sternum prolongs the recovery period of the patient.

Computer Motion of Goleta, Calif. provides a system under the trademark ZEUS that allows a surgeon to perform a minimally invasive CABG procedure. The procedure is performed with instruments that are inserted through small incisions in the patient's chest. The instruments are controlled by robotic arms. Movement of the robotic arms and actuation of the instrument end effectors are controlled by the surgeon through a pair of handles and a foot pedal that are coupled to an electronic controller.

When performing a coronary procedure it is desirable to stabilize the heart. A heart stabilizer can be provided to limit the movement of the heart at the surgical site to reduce the complexity of performing the coronary procedure. To date there has not been developed a heart stabilizer that can be used in a minimally invasive procedure. A minimally invasive heart stabilizer must have enough dexterity to be maneuvered within the chest cavity of the patient.

There have been developed articulate retractors that are used in open-heart surgery. The articulate retractors have a pair of wrist joints that allow pivotally movement of a retractor relative to a handle shaft. The joints are spatially separated such that manipulation of the retractor is cumbersome and would be impractical for use in a minimally invasive procedure. It would therefore be desirable to provide a heart stabilizer that can be used in a minimally invasive procedure.

SUMMARY OF THE INVENTION

One embodiment of the present invention is a heart stabilizer that may include a wrist which couples an end effector to a first linkage. The end effector and wrist may be inserted through an incision in the chest of a patient to assist in performing a minimally invasive coronary procedure.

BRIEF DESCRIPTION OF THE DRAWINGS

FIG. 2 is a perspective view of an embodiment of a heart stabilizer of the present invention;

FIG. 3 is an enlarged view of an elbow of the heart stabilizer;

FIG. 4 is an enlarged view of an end effector of the heart stabilizer;

FIG. 6 is a bottom perspective view of the end effector;

FIG. 7 is a bottom exploded view of the end effector;

FIG. 8 is a side view of the heart stabilizer;

FIG. 9 is a bottom view of the heart stabilizer;

DETAILED DESCRIPTION

Figure 1:
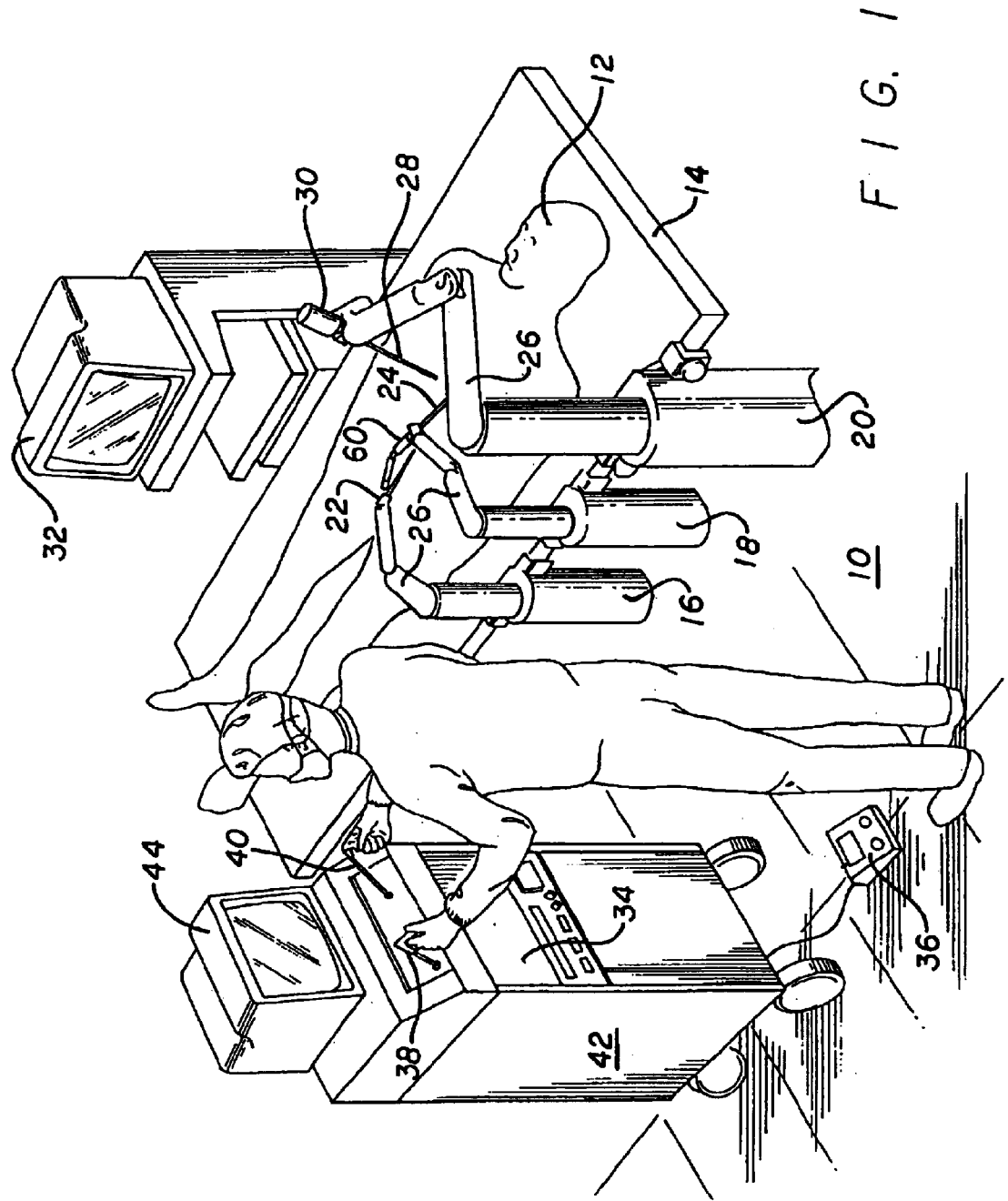
FIG. 1 is a perspective view of an embodiment of a minimally invasive surgical system of the present invention.

Referring to the drawings more particularly by reference numbers, FIG. 1 shows a system 10 that can perform minimally invasive surgery. In the preferred embodiment, the system 10 is used to perform a minimally invasive coronary artery bypass graft (MI-CABG) and other anastomostic procedures. Although a MI-CABG procedure is shown and described, it is to be understood that the system may be used for other surgical procedures. For example, the system can be used to suture any pair of vessels.

The system 10 can be used to perform a procedure on a patient 12 that is typically lying on an operating table 14. Mounted to the operating table 14 is a first articulate arm 16, a second articulate arm 18 and a third articulate arm 20. The articulate arms 16, 18 and 20 are preferably mounted to the table 14 so that the arms are at a same reference plane as the patient. Although three articulate arms are shown and described, it is to be understood that the system may have any number of arms.

The first and second articulate arms 16 and 18 each have a surgical instrument 22 and 24, respectively, coupled to a robotic arm 26, respectively. The third articulate arm 20 has an endoscope 28 that is held by a robotic arm 26. The instruments 22 and 24, and endoscope 28 are inserted through incisions cut into the skin of the patient. The endoscope has a c that is coupled to a television monitor 32 which displays images of the internal organs of the patient.

The first 16, second 18, and third 20 articulate arms are coupled to a controller 34 which can control the movement of the arms. The controller 34 is connected to an input device 36 such as a foot pedal that can be operated by a surgeon to move the location of the endoscope 28. The surgeon can view a different portion of the patient by depressing a corresponding button(s) of the pedal 36. The controller 34 receives the input signal(s) from the foot pedal 36 and moves the robotic arm 26 and endoscope 28 in accordance with the input commands of the surgeon. The robotic arms 26 may be devices that are sold by the assignee of the present invention, Computer Motion, Inc. of Goleta, Calif. under the trademark AESOP. The system is also described in U.S. Pat. No. 5,657,429 issued to Wang et al., which is hereby incorporated by reference. Although a foot pedal 36 is shown and described, it is to be understood that the system may have other input means such as a hand controller, or a speech recognition interface.

The instruments 22 and 24 of the first 16 and second 18 articulate arms, respectively, are controlled by a pair of master handles 38 and 40 that can be manipulated by the surgeon. The handles 38 and 40, and arms 16 and 18, have a master-slave relationship so that movement of the handles 38 and 40 produces a corresponding movement of the surgical instruments. The handles 38 and 40 may be mounted to a portable cabinet 42. A second television monitor 44 may be placed onto the cabinet 42 and coupled to the endoscope 28 so that the surgeon can readily view the internal organs of the patient. The handles 38 and 40 are also coupled to the controller 34. The controller 34 receives input signals from the handles 38 and 40, computes a corresponding movement of the surgical instruments, and provides output signals to move the robotic arms and instruments. The entire system may be a product marketed by Computer Motion under the trademark Zeus. The operation of the system is also described in U.S. Pat. No. 5,762,458 issued to Wang et al. and assigned to Computer Motion, which is hereby incorporated by reference. The system may also include a heart stabilizer 60 that is used to perform minimally invasive coronary procedures. The stabilizer 60 is typically inserted through an incision of the patient's chest. The stabilizer 60 can be held by a robotic arm or a static structure (not shown).

FIGS. 2–14 show an embodiment of a heart stabilizer 60. Referring to FIGS. 2, 8 and 9, the heart stabilizer 60 may comprise a wrist 62 that couples an end effector 64 to a first linkage 66. The wrist 62 allows the end effector 64 to be moved relative to the first linkage 66. The first linkage 66 may be coupled to a second linkage 68 by an elbow 70. The elbow 70 allows the first linkage 66 to be moved relative to the second linkage 68. The wrist 62 and elbow 70 allow the end effector 64 to be accurately located within the chest cavity of a patient. Each linkage 66 and 68 may be a cannula with an inner longitudinal channel.

As shown in FIGS. 3 and 4 the elbow 70 and wrist 62 may have a plurality of universal joints 72 and 74, respectively, that provides three degrees of freedom. At least two universal joints 72 of the wrist 62 may pivot about the same plane to minimize the relative movement of one joint pivot point relative to another joint pivot point. Relative pivot point movement can increase the complexity of positioning the end effector 64. Likewise, two or more universal joints 74 of the elbow 70 can pivot about the same plane.

Referring to FIGS. 5, 6, 7, 10, 11 and 12, the end effector 64 may have a pair of paddles 76 that can move relative to a gear housing 78. Each paddle 76 may have an opening 80 that is in fluid communication with a rigid tube 82. Each rigid tube 82 may be connected to a flexible tube 84. The flexible tubes 84 may be connected to a source of vacuum (not shown) that can create a vacuum pressure at the openings 80. The flexible tubes 84 can be routed along channels 86 of the first linkage 66, as shown in FIGS. 2 and 4, to minimize the profile of the stabilizer 60. Although suction paddles are shown and described, it is to be understood that the heart stabilizer 60 may be used without a suction system.

Figure 5:
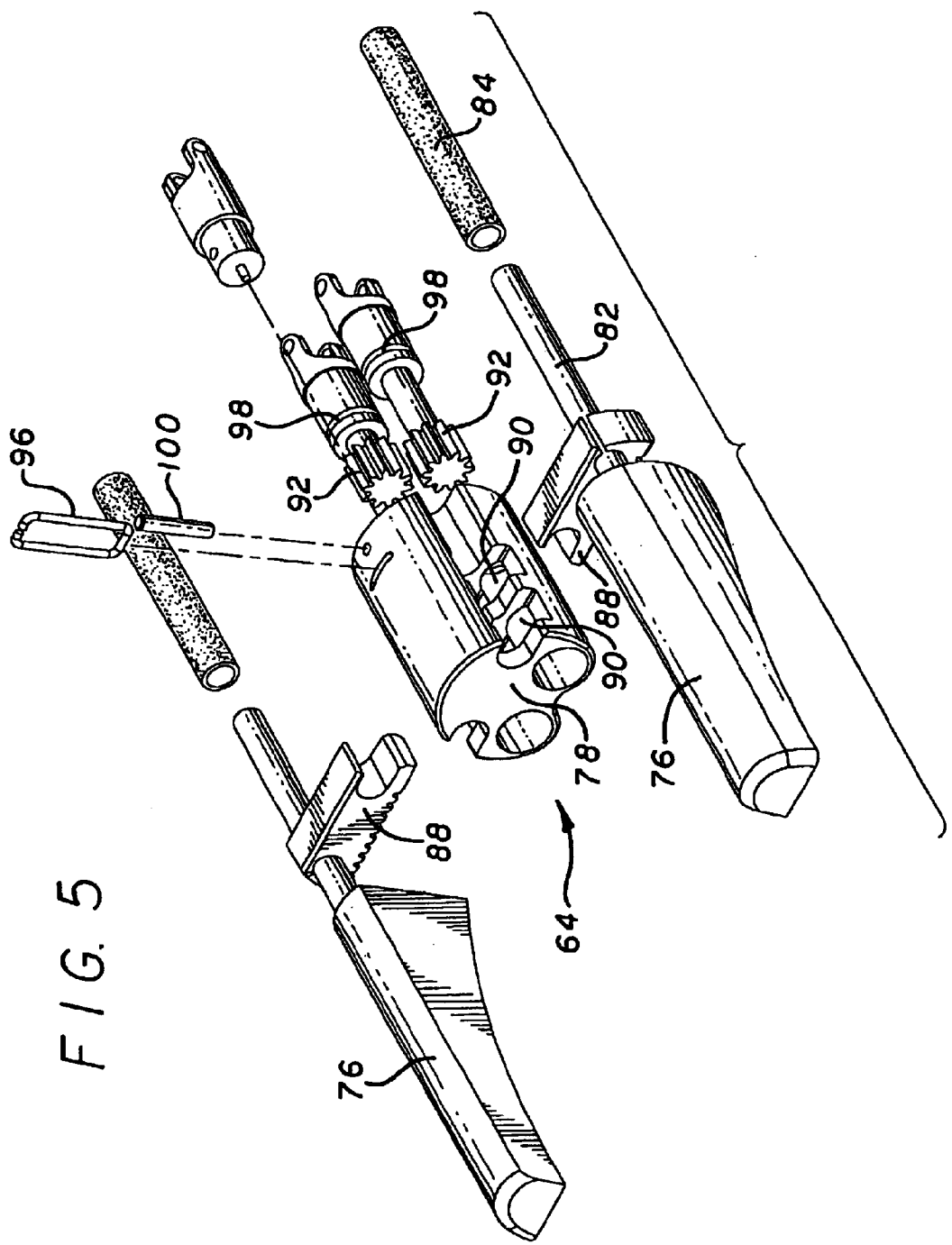
FIG. 5 is an exploded view of the end effector.
Figure 11:
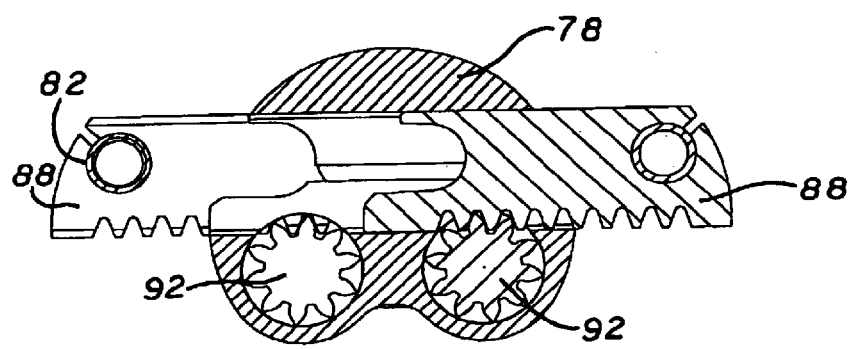
FIG. 11 is a sectional view taken at line 11—11 of FIG. 10.
Figure 10:
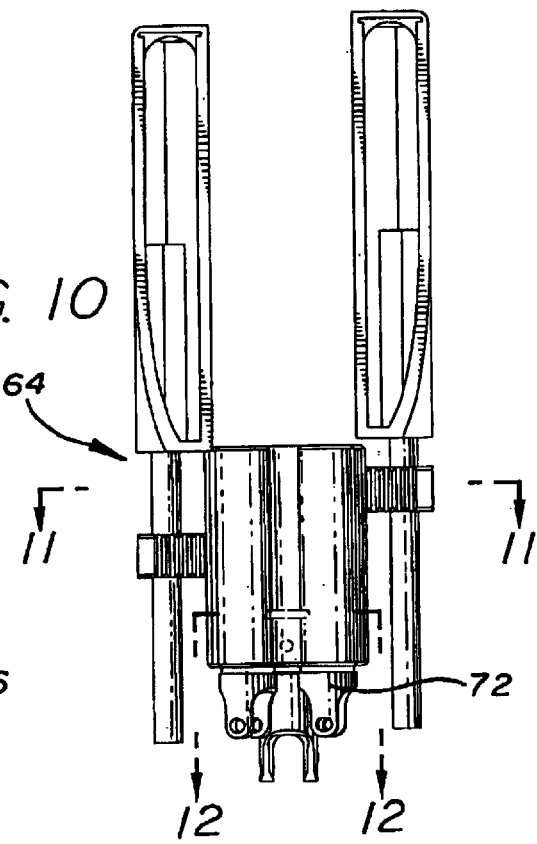
FIG. 10 is a bottom view of the end effector.
Figure 12:
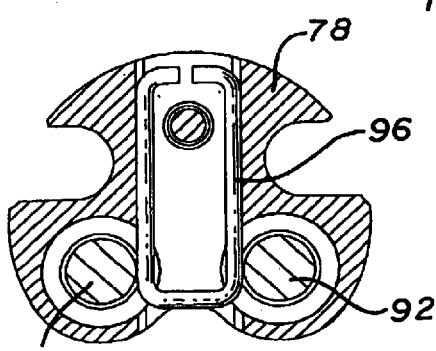
FIG. 12 is a sectional view taken at line 12—12 of FIG. 10.

Each rigid tube 84 may be connected to a gear rack 88. Each gear rack 88 can move within corresponding channels 90 of the gear housing 78. The gear racks 90 may be coupled to corresponding pinion gears 92 attached to two of the universal joints 72 of the wrist 62. The universal joints 72 may be connected to a pair of drive shafts 94 that extend through the first linkage 66 as shown in FIGS. 2, 3 and 4. Rotation of the drive shafts 94 will rotate the pinion gears 92 and translate the corresponding gear racks 88 and paddles 76 in an inward or outward direction. The movement of the paddles 76 occurs without disturbing the relative position of the end effector 64 to the first linkage 66. As shown in FIGS. 5, 7 and 12, the end effector 64 may include a spring clip 96 that is inserted into corresponding annular grooves 98 of the pinion gears 92 and captures the gears 92 within the gear housing 78. The end effector 64 may also have a pin 100 that is inserted into a corresponding aperture 102 of the other universal joint 72 to capture the joint 72 within the gear housing 78.

Figure 13:
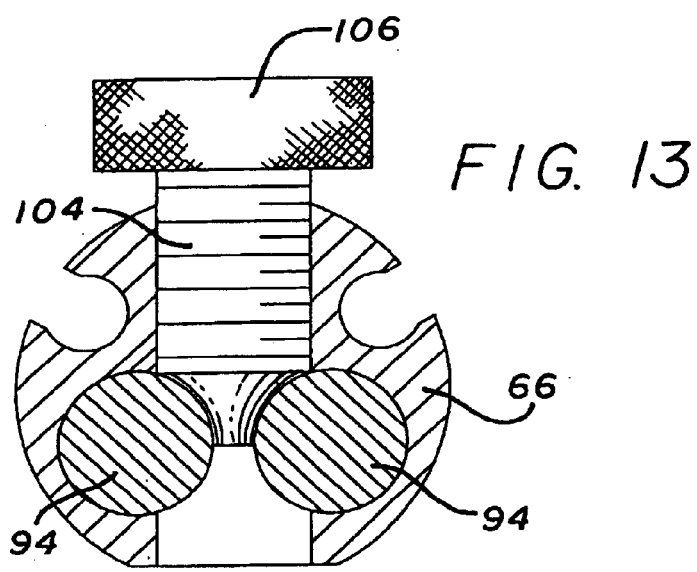
FIG. 13 is a sectional view taken at line 13—13 of FIG. 2.

As shown in FIG. 13, the heart stabilizer 60 may include a locking pin 104 that can be pressed into the drive shafts 94 to prevent rotation of the shafts 94. Impeding shaft rotation locks the position of the wrist 62, elbow 70 and paddles 76. A surgeon may lock and unlock the wrist 62, elbow 70 and paddles 76 by rotating a head 106 of the pin 104.

Figure 14:
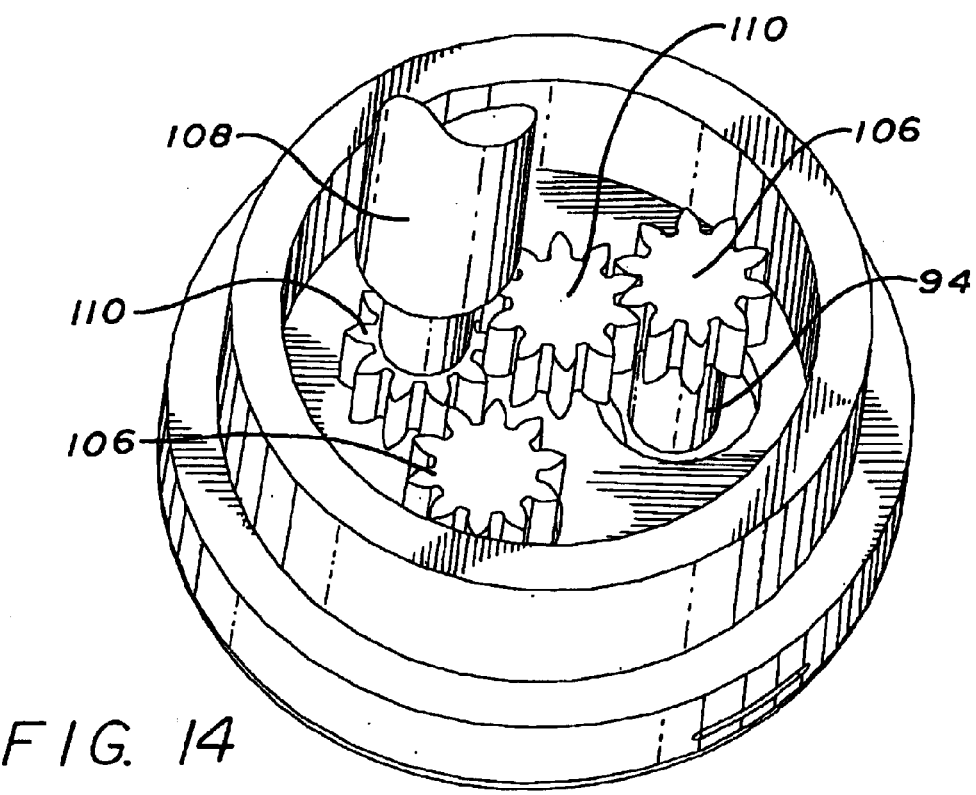
FIG. 14 is a sectional view taken at line 14—14 of FIG. 2.

As shown in FIG. 14, each drive shaft 94 may have a pinion gear 106 that is coupled to an output shaft 108 of a motor (not shown) by a pair of coupling gears 110. Rotation of the output shaft 108 rotates the drive shafts 94 and moves the paddles 76. The motor is preferably reversible so that the paddles 76 can be moved inward or outward. The motor may be connected to the controller 34 and foot pedal 36 shown in FIG. 1. The surgeon can move the paddles 76 inward or outward by depressing a corresponding switch(es) of the foot pedal 36. Alternatively, the motor can be actuated through voice recognition.

Figure 15:
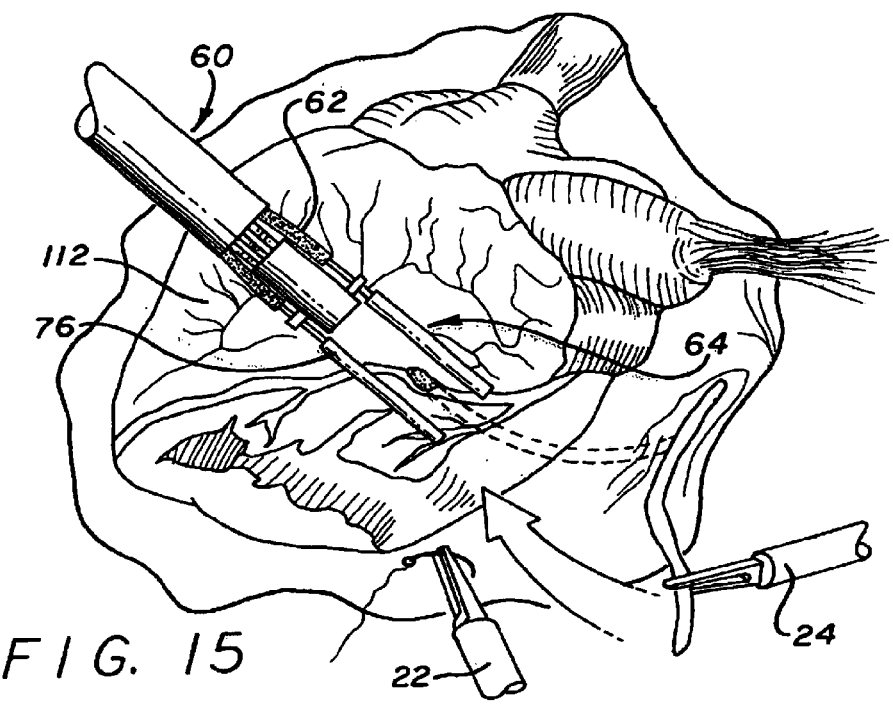
FIG. 15 is a top view showing the heart stabilizer fastened to a heart.
Figure 16:
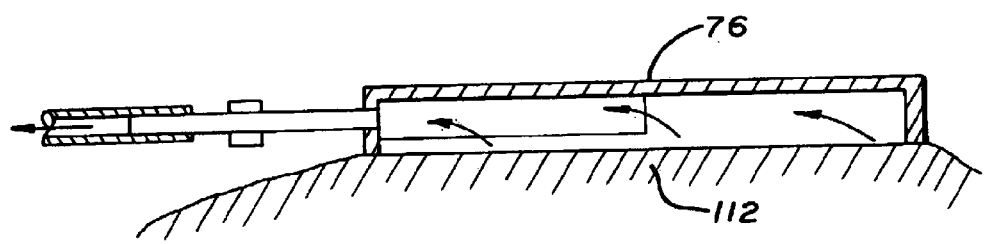
FIG. 16 is a side view of the heart stabilizer fastened to the heart.

As shown in FIGS. 15 and 16, the end effector 64 and wrist 62 can be inserted into the patient's chest cavity adjacent to the heart 112. The surgeon can view the location of the end effector 64 relative to the heart 112 on the monitor 32 shown in FIG. 1. The surgeon can grasp the second linkage 66 and move the stabilizer 60 until the end effector 64 is correctly located on the heart 112. The drive motor can then activated to move the paddles 76 to the desired location. The surgeon may then turn the locking pin to secure the position of the stabilizer 60 relative to the patient.

As shown in FIG. 16, the vacuum source may be activated to pull the heart 112 into the paddles 76. The stabilizer 60 will then prevent movement of the adjoining area of the heart while the surgeon performs a coronary procedure with the surgical instruments 22 and 24. After the procedure is completed, the stabilizer 60 can be removed by terminating the vacuum and pulling the end effector 64 out of the chest cavity.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although the medical device shown in FIGS. 2–14 has been shown and described as a heart stabilizer, it is to be understood that the device can be used as a retractor. The paddles 76 can be used, or modified to be used, as rectractor jaws.

What is claimed is:

1. A heart stabilizer, comprising:
   an end effector;
   a first linkage; and,
   a wrist that couples said first linkage to said end effector to allow said end effector to move from a position essentially parallel with said first linkage to a position at an angle oblique to said first linkage.

2. The heart stabilizer of claim 1, wherein said end effector includes a paddle.

3. The heart stabilizer of claim 2, wherein said paddle includes an opening that is adapted to be coupled to a source of vacuum.

4. The heart stabilizer of clam 1, wherein said end effector includes a rack, and a pinion gear that is coupled to said rack.

5. The heart stabilizer of claim 1, wherein said wrist includes a first universal joint.

6. The heart stabilizer of claim 5, wherein said wrist includes a second universal joint that pivots about a common plane with said first universal joint.

7. The heart stabilizer of claim 4, further comprising a drive shaft that is coupled to said rack and extends along said first linkage.

8. The he art stabilizer of claim 7, further comprising a motor output shaft that is coupled to said drive shaft.

9. The heart stabilizer of claim 7, further comprising locking pin that is coupled to said drive shaft.

10. The heart stabilizer of claim 1, further comprising a second linkage and an elbow that are coupled to said first linkage.

11. The heart stabilizer of claim 10, wherein said elbow includes a first universal joint.

12. A heart stabilizer, comprising:
    a first linkage that has a proximal end and a distal end;
    an elbow coupled to said proximal end of said first linkage;
    a wrist coupled to said distal end of said first linkage;
    an end effector coupled to said wrist, said end effector having a paddle; and,
    a drive shaft that extends along said first linkage and is coupled to said paddle of said end effector to move said paddle.

13. The heart stabilizer of claim 12, wherein said paddle includes an opening that is adapted to be coupled to a source of vacuum.

14. The heart stabilizer of claim 12, wherein said end effector includes a rack, and a pinion gear that is coupled to said rack.

15. The heart stabilizer of claim 12, wherein said wrist includes a first universal joint.

16. The heart stabilizer of claim 15, wherein said wrist includes a second universal joint that pivots about a common plane with said first universal joint.

17. The heart stabilizer of claim 12, further comprising a motor output shaft that is coupled to said drive shaft.

18. The heart stabilizer of claim 12, further comprising locking pin that is coupled to said drive shaft.

19. The heart stabilizer of claim 12, wherein said elbow includes a first universal joint.

20. A method for applying a heart stabilizer to a heart of a patient that has a chest, comprising:
    inserting an end effector and a wrist through an incision in the chest of the patient, the wrist couples the end effector to a first linkage;
    bending the wrist to place the end effector onto the heart; and,
    bending the wrist to move the end effector from a position essentially parallel with the first linkage to a position at an angle oblique to the first linkage.

21. The method of claim 20, further comprising bending an elbow to place the end effector onto the heart.

22. The method of claim 20, further comprising moving a paddle of the end effector relative to the heart.

23. A retractor, comprising:
    a first linkage;
    an end effector;
    a first joint that couples said end effector to said first linkage;
    a second joint that couples said end effector to said first linkage and pivots about a common plane with said first joint.

24. The retractor of claim 23, where in said end effector includes a paddle.

25. The retractor of claim 24, wherein said paddle includes an opening that is adapted to be coupled to a source of vacuum.

26. The retractor of claim 23, wherein said end effector includes rack, and a pinion gear that is coupled to said rack.

27. The retractor of claim 26, further comprising a drive shaft that is coupled to said rack and extends along said first linkage.

28. The retractor of claim 27, further comprising a motor output shaft that is coupled to said drive shaft.

29. The retractor of claim 27, further comprising a locking pin that is coupled to said drive shaft.

30. The retractor of claim 27, further comprising a second linkage and an elbow that are coupled to said shaft.

31. The retractor of claim 30, wherein said elbow includes a first universal joint.

* * * * *

UNITED STATES PATENT AND TRADEMARK OFFICE
CERTIFICATE OF CORRECTION

PATENT NO. : 6,936,001 B1
APPLICATION NO. : 09/411442
DATED : August 30, 2005
INVENTOR(S) : Edward Ramsey Snow It is certified that error appears in the above-identified patent and that said Letters Patent is hereby corrected as shown below:

Cancel claims 1-31, and add the following:

Claims:

1. A heart stabilizer, comprising:
    an end effector having at least two paddles in parallel alignment with each other which are translatable toward or away from each other while maintaining parallel alignment;
    a first linkage; and,
    a wrist that couples said first linkage to said end effector to allow said and effector to move from a position essentially parallel with said first linkage to a position at an angle oblique to said first linkage.

2. The heart stabilizer of claim 1, wherein at least one of the said at least two paddles includes an opening that is adapted to be coupled to a source of vacuum.

3. The heart stabilizer of claim 1, wherein said end effector includes a rack, and a pinion gear that is coupled to said rack.

4. The heart stabilizer of claim 1, wherein said wrist includes a first universal joint.

5. The heart stabilizer of claim 4, wherein said wrist includes a second universal joint that pivots about a common plane with said first universal joint.

6. The heart stabilizer of claim 3, further comprising a drive shaft that is coupled to said rack and extends along said first linkage.

7. The heart stabilizer of claim 6, further comprising a motor output shaft that is coupled to said drive shaft.

Signed and Sealed this
Thirtieth Day of October, 2012

David J. Kappos
*Director of the United States Patent and Trademark Office*

8. The heart stabilizer of claim 6, further comprising a locking pin that is coupled to said drive shaft.

9. The heart stabilizer of claim 1, further comprising a second linkage and an elbow that are coupled to said first linkage.

10. The heart stabilizer of claim 9, wherein said elbow includes a first universal joint.

11. A heart stabilizer, comprising:
a first linkage that has a proximal end and a distal end;
an elbow coupled to said proximal end of said first linkage;
a wrist coupled to said distal end of said first linkage;
an end effector coupled to said wrist, said end effector having at least two paddles in parallel alignment with each other; and,
a drive shaft that extends along said first linkage and is coupled to said at least two paddles of said end effector to move said at least two paddles toward or away from each other while maintaining parallel alignment.

12. The heart stabilizer of claim 11, wherein at least one of said at least two paddles includes an opening that is adapted to be coupled to a source of vacuum.

13. The heart stabilizer of claim 11, wherein said end effector includes a rack, and a pinion gear that is coupled to said rack.

14. The heart stabilizer of claim 11, wherein said wrist includes a first universal joint.

15. The heart stabilizer of claim 14, wherein said wrist includes a second universal joint that pivots about a common plane with said first universal joint.

16. The heart stabilizer of claim 11, further comprising a motor output shaft that is coupled to said drive shaft.

17. The heart stabilizer of claim 11, further comprising a locking pin that is coupled to said drive shaft.

18. The heart stabilizer of claim 11, wherein said elbow includes a first universal joint.

19. A method for applying a heart stabilizer to a heart of a patient that has a chest, comprising:
providing the heart stabilizer having an end effector and a wrist, wherein the end effector includes at least two paddles in parallel alignment with each other;
inserting the end effector and the wrist through an incision in the chest of the patient wherein the wrist couples the end effector to a first linkage;
translating at least one of the at least two paddles toward or away from another of the at least two paddles while maintaining parallel alignment;
bending the wrist to place the end effector onto the heart; and, bending the wrist to move the end effector from a position essentially parallel with the first linkage to a position at an angle oblique to the first linkage.

20. The method of claim 19, further comprising bending an elbow to place the end effector onto the heart.

21. A retractor, comprising:
a first linkage;
an end effector having at least two paddles in parallel alignment with each other which are translatable toward or away from each other while maintaining parallel alignment;
a first joint that couples said end effector to said first linkage; and
a second joint that couples said end effector to said first linkage and pivots about a common plane with said first joint.

22. The retractor of claim 21, wherein at least one of said at least two paddles includes an opening that is adapted to be coupled to a source of vacuum.

23. The retractor of claim 21, wherein said end effector includes a rack, and a pinion gear that is coupled to said rack.

24. The retractor of claim 23, further comprising a drive shaft that is coupled to said rack and extends along said first linkage.

25. The retractor of claim 24, further comprising a motor output shaft that is coupled to said drive shaft.

26. The retractor of claim 24, further comprising a locking pin that is coupled to said drive shaft.

27. The retractor of claim 24, further comprising a second linkage and an elbow that are coupled to said shaft.

28. The retractor of claim 27, wherein said elbow includes a first universal joint.

29. The heart stabilizer of claim 4, wherein the end effector further includes a rack and a pinion gear coupled to said rack, wherein the rack and pinion gear are disposed distal to the first universal joint.

30. The heart stabilizer of claim 14, wherein the end effector includes a rack and a pinion gear that is coupled to said rack, wherein the rack and pinion gear are disposed distal to the first universal joint.

31. The retractor of claim 23, wherein said rack and pinion gear are disposed distal to the first joint.